(«12») United States Patent
Schaefer et al.

(10) Patent No.: US 9,494,181 B2
(45) Date of Patent: Nov. 15, 2016

(54) HIGH TEMPERATURE SECONDARY TORQUE RETENTION FOR BOLTED ASSEMBLIES

(71) Applicant: General Electric Company, Schenectady, NY (US)

(72) Inventors: Thomas Dean Schaefer, West Milwaukee, WI (US); Gregory Alan Steinlage, West Milwaukee, WI (US); Donald Robert Allen, Waukesha, WI (US); Evan Michael Lampe, West Milwaukee, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 375 days.

(21) Appl. No.: 14/106,066

(22) Filed: Dec. 13, 2013

(65) Prior Publication Data
US 2015/0167724 A1    Jun. 18, 2015

(51) Int. Cl.
| | |
|---|---|
| *F16B 19/00* | (2006.01) |
| *F16B 39/24* | (2006.01) |
| *F16B 43/00* | (2006.01) |
| *H01J 35/16* | (2006.01) |
| *H01J 35/22* | (2006.01) |
| *F16B 5/02* | (2006.01) |
| *F16B 39/284* | (2006.01) |
| *A61B 6/00* | (2006.01) |

(52) U.S. Cl.
CPC ............ *F16B 39/24* (2013.01); *F16B 5/0241* (2013.01); *F16B 43/00* (2013.01); *H01J 35/16* (2013.01); *A61B 6/40* (2013.01); *F16B 5/0258* (2013.01); *F16B 39/284* (2013.01); *F16B 43/001* (2013.01); *H01J 35/22* (2013.01); *H01J 2235/165* (2013.01); *H01J 2235/167* (2013.01)

(58) Field of Classification Search
CPC .. F16B 39/284; F16B 43/001; F16B 5/0258; F16B 43/00; H01J 35/22; H01J 35/16; H01J 2235/165; H01J 2235/167; A61B 6/40
USPC ....... 411/360, 369, 371.1, 540, DIG. 2, 969, 411/967, 533, 82
See application file for complete search history.

(56) References Cited

U.S. PATENT DOCUMENTS

| | | | | |
|---|---|---|---|---|
| 3,202,033 | A | * | 8/1965 | Weidner, Jr. .............. B26F 1/02 277/644 |
| 3,500,712 | A | * | 3/1970 | Wagner ................. F16B 43/001 411/369 |

(Continued)

*Primary Examiner* — Chi Q Nguyen
(74) *Attorney, Agent, or Firm* — GE Global Patent Operation; Marc A. Vivenzio

(57) ABSTRACT

A fastening assembly includes a fastener having a head with an underside and an elongated shaft extending therefrom. The fastener constructed of at least one of a refractory metal and a superalloy. A washer includes a body with an upper surface and an opposing lower surface which defines opening portion for receiving the elongated shaft of the fastener therethrough. The upper surface of the washer forms diffusion bonds with the underside of the head of the fastener when the washer and the fastener are held in contact at temperatures in excess of 500° C.

17 Claims, 4 Drawing Sheets

(56) References Cited

U.S. PATENT DOCUMENTS

| | | | | |
|---|---|---|---|---|
| 3,539,875 A | * | 11/1970 | Harrington | H01L 23/4006 257/731 |
| 4,292,876 A | * | 10/1981 | De Graan | F16B 43/001 411/369 |
| 4,747,739 A | * | 5/1988 | Bowman | B22D 7/08 249/174 |
| 4,987,714 A | * | 1/1991 | Lemke | E04D 3/3603 411/369 |
| 5,069,589 A | * | 12/1991 | Lemke | E04D 5/145 411/160 |
| 2002/0187020 A1 | * | 12/2002 | Julien | F16B 1/0014 411/544 |
| 2005/0178816 A1 | * | 8/2005 | Stevenson | B21J 15/027 228/112.1 |
| 2008/0247843 A1 | * | 10/2008 | Shluzas | F16B 15/06 411/369 |
| 2015/0192031 A1 | * | 7/2015 | Sun | C22C 14/00 416/241 R |

\* cited by examiner

HIGH TEMPERATURE SECONDARY TORQUE RETENTION FOR BOLTED ASSEMBLIES

BACKGROUND OF THE INVENTION

High energy x-ray tubes are used in medical device applications to provide an x-ray source. The materials in the x-ray tube are subject to high temperatures during the operation of the x-ray tube. The x-rays generated by the x-ray tube are directed out of a window toward a target such as portion of a patient. The x-ray tube is subject to high temperatures when the x-ray tube is generating x-rays and then cools. A heat shield may be secured to a portion of the x-ray tube to shield the window from backscattered electrons.

SUMMARY OF THE INVENTION

A fastening assembly includes a fastener having a head with an underside and an elongated shaft extending therefrom. The fastener constructed of at least one of a refractory metal and a superalloy. A washer includes a body with an upper surface and an opposing lower surface which defines opening portion for receiving the elongated shaft of the fastener therethrough. The upper surface of the washer forms diffusion bonds with the underside of the head of the fastener when the washer and the fastener are held in contact at temperatures in excess of 500° C.

In another embodiment, an assembled structure suitable for use at high temperatures includes at least two bolts. Each bolt includes a head with an underside and an elongated shaft extending from the underside. Each bolt is constructed of at least one of a refractory metal and a superalloy. A washer includes a body with an upper surface and an opposing lower surface defining at least a first aperture and a second aperture respectively receiving the shaft of at least the first bolt and the shaft of the second bolt. The assembled structure also includes a first high temperature material into which the at least two bolts have been threaded and a second high temperature material which has been secured to the first high temperature material by the at least two bolts. The underside of the head of each bolt has mechanically measurably diffusion bonded to the upper surface of the washer.

In yet another embodiment a process for securing a heat shield for the insert window of a high energy X-ray tube to a collector for back scattered electrons includes providing a fastener having a head with a member extending therefrom, the member comprising at least one of a refractory metal and a superalloy. The process also includes providing a washer having a body with an upper surface and an opposing lower surface which defines at least a first opening for receiving the member of the fastener therethrough. The process further includes passing the fastener through the first opening of the washer and securing the member to a threading the fastener into a first member. The process also includes subjecting the assembled structure to a high temperature to cause the fastener to diffusion bond to the washer to a mechanically detectable degree.

DETAILED DESCRIPTION OF THE PREFERRED EMBODIMENTS

Figure 1:
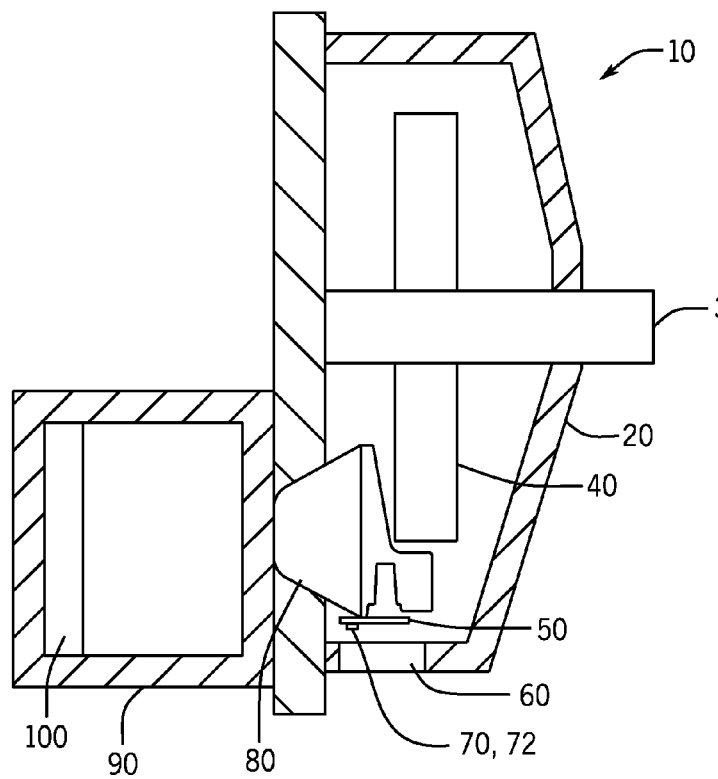
FIG. 1 is a schematic of the internal structure of the insert of a high energy X-ray tube with a rotating anode target.

Referring to FIG. 1, the internal structure 10 of the insert of a high energy X-ray tube has a rotating anode target 40 mounted on a bearing 30 that is supported by a frame 20. A cathode 100 in a housing 90 supplies electrons which are accelerated by a high electrical potential and strike a focus area on the target 40 causing the generation of X-rays. These X-rays are directed out of a window 60 constructed of a material translucent to X-rays such as beryllium. However, not all of the accelerated electrons are absorbed by the target 40 and a collector 80 is provided to absorb many of these backscattered electrons. Some of these backscattered electrons follow the path of the exiting X-rays and strike the window 60. This subjects the window 60 to thermal stresses that can reduce the operating life of the insert. The window 60 is sealed to the envelope of the insert to maintain an effective vacuum inside the insert. However, the heating and cooling of the window 60, as the X-ray tube is cycled through a duty cycle of generating X-rays and then being off until the next exposure is called for, causes the window to expand and contract. This expansion and contraction is not precisely matched to that of the wall of the envelope for various reasons and the mismatch causes stress upon the seal that over time can cause it to fail. The heating of the window 60 is ameliorated by interposing a heat shield 50 in the path of backscattered electrons to absorb some of them that would otherwise strike the window 60. The heat shield is constructed of a material, such as graphite, beryllium, or titanium, which can absorb these backscattered electrons without unduly interfering with the transmission of X-rays. This material, for instance graphite, may lack the ability to undergo much elastic compression and, in fact, may be subject to crushing upon tightening of the bolts 70, 72. Heat shield 50 is constructed of a material that is capable of operating in a high temperature environment such as over 500° C. and has high heat conduction. Heat shield 50 absorbs heat and radiates it out. Heat shield 50 is made with graphite or another material that permits x-rays to be transmitted therethrough minimizing effects on image quality as compared to a heat shield made of metals that deflect and/or absorb x-rays compromising image quality. The heat shield is secured in place by bolts 70 and 72 that are threaded in to the collector 80. The bolts 70 and 72 and the collector 80 are constructed of a material, such as a molybdenum alloy like TZM (A well known and commonly used alloy of titanium, zirconium and molybdenum), or other refractory metals that are used at operating temperatures in excess of about 500° C. and in a temperature region between 500° C. and 1500° C. Other materials for the bolts that have similar operating characteristics to the refractory metals as noted herein are also contemplated. For example, austenitic nickel-chromium based superalloys or other high temperature superalloys are contemplated as well. Superalloys may include certain nickel alloys. Of course other temperature ranges are also contemplated. In one embodiment the operating temperatures will be excess of about 400° C., and in another embodiment the operating temperatures will be in excess of about 300° C. In a further embodiment the operating temperature will be between 300° C. and 1500° C. and in another embodiment the operating temperature will be between 400° C. and 1500° C. In still another embodiment, the operating temperature range will be between 600° C. and 1200° C. In another embodiment the operating temperature range will include the range of 700° C. and 900° C. All of the temperature notations used herein are in degrees Celsius.

Figure 2:
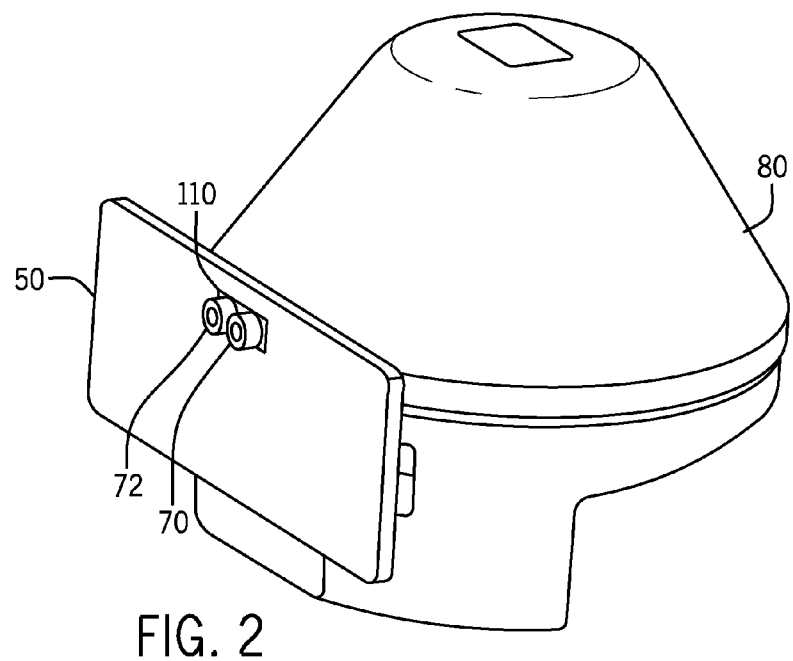
FIG. 2 is a perspective view of a backscatter electron collector with a heat shield bolted to it across the X-ray exit path.

Referring to FIG. 2, the heat shield 50 has been bolted to an appropriate place on the collector 80 with bolts 70 and 72. The bolts 70 and 72 have been passed through a common washer 110 that has an aperture for the elongated shaft of each bolt. However other types of washer designs are also contemplated, such as a washer that has a region with a first opening and a second opening, where the openings are connected to one another, separated from one another and/or are completely surrounded by the washer body or only partially surrounded by the washer body. The head of each bolt has been snugged against the washer 110 by threading the bolt into the collector 80 such that the underside of the head is in firm contact with the top surface of the washer 110. The bottom surface of the washer 110 then abuts the top surface of the heat shield 50. The bottom surface of the heat shield 50 in turn abuts the collector 80. The washer 110 is constructed of a material, such as nickel, cobalt or iron or alloys thereof, that provide diffusion bonds to the underside of the heads of the bolts 70 and 72 under appropriate conditions of time and temperature such as temperatures in excess of about 500° C. and times in excess of thirty minutes. Of course other temperature and time combinations that provide diffusion bonds are contemplated. In one embodiment the washer material is different than the bolt material. However, the washer material may be the same as the bolt material if diffusion bonds are created as described herein. In an alternative embodiment an intermediate material may be placed between the washer and the bolt to assist in the creation of a diffusion bond. In yet another embodiment, a material may be provided on the threaded portion of the bolts and/or within the threaded region of the collector to provide a diffusion bond between the threaded region of the bolts and the threaded region of the collector. In one embodiment nickel is the intermediate material applied to the threads of the bolts and/or the collector. Other materials that would provide for diffusion bonds between the bolts and collector are contemplated in this alternative embodiment. The inclusion of diffusion bonds between the bolt threads and the threads of the collector provide for additional torque retention between the bolts and collector and make removing the bolts from the collector more difficult if there is a need to repair the x-ray tube structure that requires removal of the bolts. In another embodiment described herein no diffusion bonds are created between the threaded portion of the bolt and the threaded portion of the collector to make removal of the bolts from the collector easier.

Figure 3:
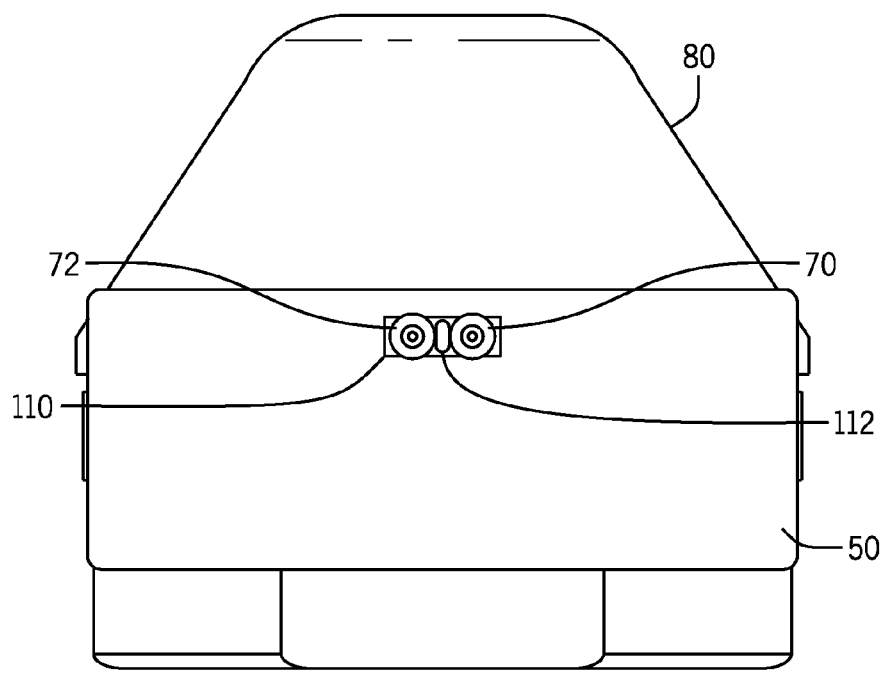
FIG. 3 is a front elevation view of a backscatter electron collector with a heat shield bolted to it.

Referring to FIG. 3, the heat shield 50 is bolted to the collector 80 by bolts 70 and 72 whose elongated shafts pass through apertures in washer 110 that has an area of weakness 112 in the region between the two apertures. When the undersides of the heads of the two bolts 70 and 72 have become bonded to the upper surface of the washer 110, this allows one of the bolts to be retracted by fracturing the washer 110 through this area of weakness 112. The area of weakness 110 is shown as the mere elimination of some of the web of the washer 110 but other means of enhancing frangibility such as scoring could also be used. In the absence of this area of weakness 112, the retraction of either bolt 70 or 72 is only possible if that bolt's diffusion bond with the washer 110 is broken. It is mechanically not possible to rotate a single bolt so as to retract it so long as both bolts are attached to the washer 110 and washer is unfractured. The washer is not free to rotate with the bolt being retracted because the other bolt has been passed through it and is still engaged in the threads of the collector 80.

Figure 4:
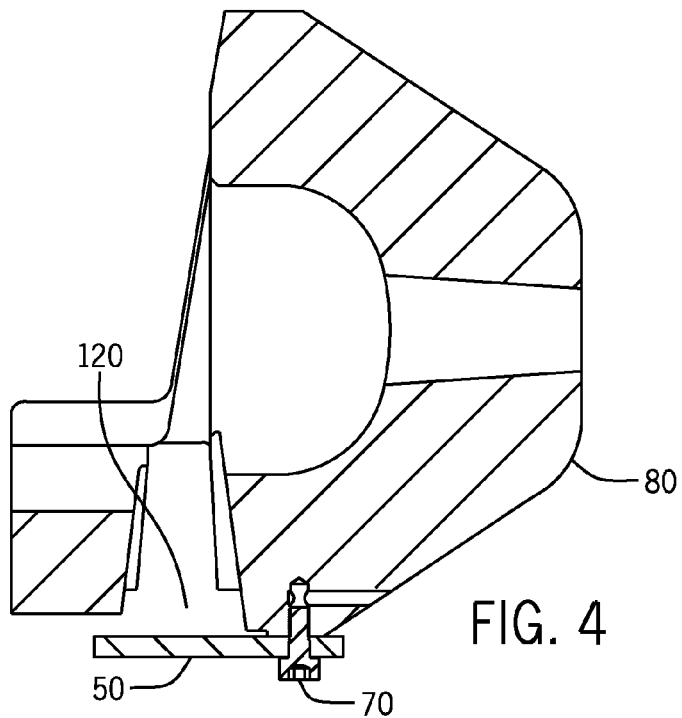
FIG. 4 is a cross section of a backscatter electron collector with a heat shield bolted to it.

Referring to FIG. 4, the heat shield 50 is held in position across the channel 120 through which X-rays pass after being generated by the collision of accelerated electrons with the rotating anode target 40 shown in FIG. 1. It is held in position by bolt 70 that is threaded into the collector 80. Neither the washer 110 nor the other bolt 72 is shown in this view.

Figure 5:
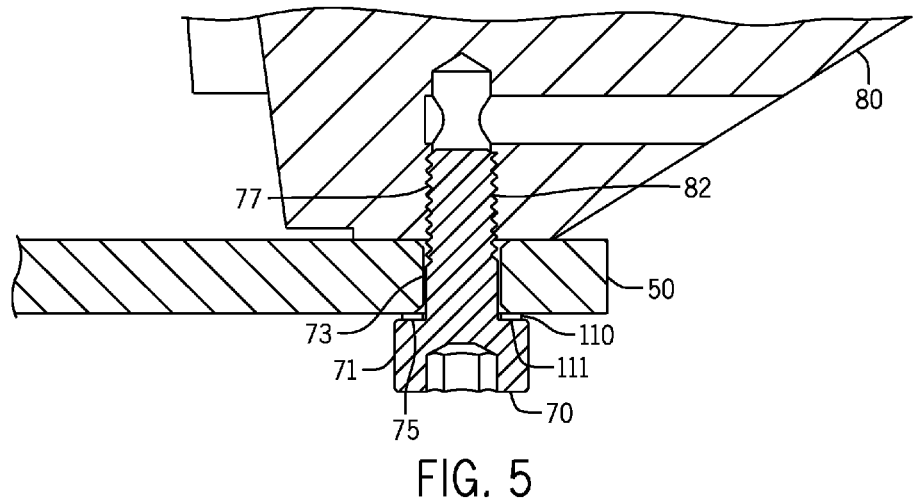
FIG. 5 is a cross section of the portion of a backscatter electron collector where a heat shield has been bolted to it.

Referring to FIG. 5, the elongated shaft 73 of the bolt 70 passes through an aperture in the washer 110 and through the heat shield 50. The threads 77 of the bolt 70 engage the threads 82 of the collector 80. The bolt 70 is tightened by threading its threads 77 into the threads 82 of the collector 80 until the underside 75 of its head 71 come in contact with the top surface 111 of the washer 110. If the heat shield 50 is constructed of a material, like graphite, that does not undergo much elastic compression, it is difficult to secure the bolt 70 against loosening by tightening it so far as to cause elastic compression on the washer. Heat shield 50 may be formed of other materials that provide similar x-ray transmission, electron absorption and high surface temperature to graphite. In other environments washers are adjacent to rigid materials that resist compression and so tightening of the bolt causes elastic compression forces that press against the head of the bolt and providing resistance to its retraction. The bolts 70 and 72 are subject to being loosened by vibration and thermal stresses such as not seeing precisely the same temperature profile as the portion of the collector into which they are threaded and not experiencing the same expansion and contraction as the heat shield 50 through which they are passed. However, at the service temperatures typically seen by the collector 80 and the bolts 70 and 72, the typical materials of construction, such as molybdenum or molybdenum alloys, do not appreciably diffusion bond across their respective threads 82 and 77. To address this situation special steps are taken so that the undersides of the heads of theses bolts, such as the underside 75 of the head 71 of bolt 70, become diffusion bonded to the upper surface 111 of the washer 110. In particular, the material of the washer 110 is selected so that it will readily diffusion bond to the underside of the bolt head and temperatures are used in manufacture to cause such diffusion bonding. As is readily apparent from FIG. 2 and FIG. 3, this means that these bolts can only be loosened by fracture of the washer 110 through its region of weakness 112 or fracture of the diffusion bonds to one of the bolts 70 and 72. In one embodiment the region of weakness 112 will break before the diffusion bonds break between the bolts and washer.

Figure 6:
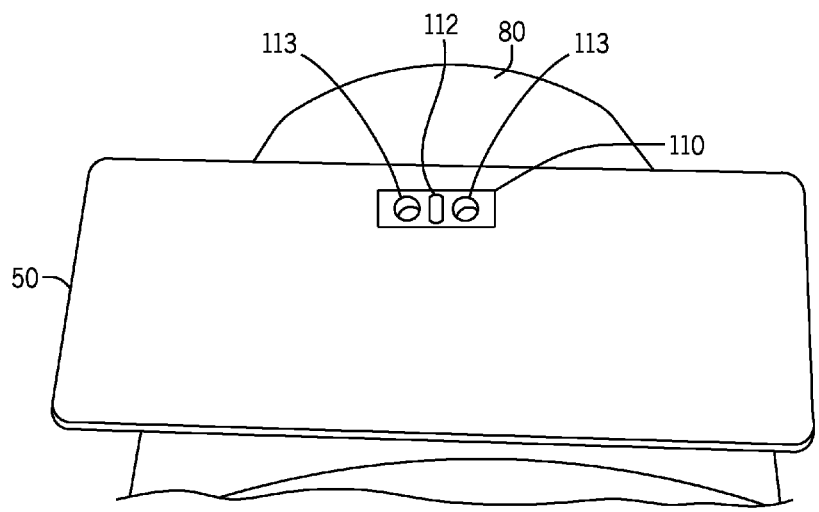
FIG. 6 is a front elevation of a heat shield in position to be bolted to a collector.

Referring to FIG. 6, the washer 110 has a region of weakness 112 between its two apertures 113 for bolts that secure the heat shield 50 to the collector 80. A substantial amount of the material of the washer has been removed to facilitate its fracture upon the application of a reverse torque to a bolt which has diffusion bonded to the washer 110.

Figure 7:
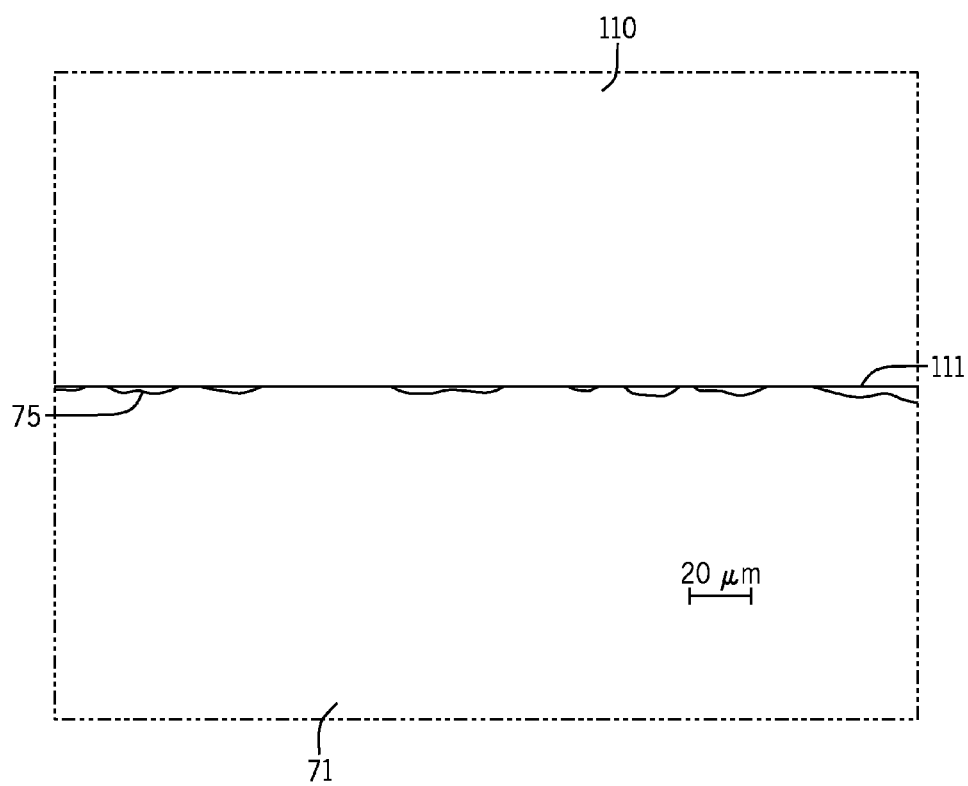
FIG. 7 is a photomicrograph of a cross section of the joint between the underside of a bolt head and a washer after diffusion bonding.

Referring to FIG. 7, diffusion bonding has occurred between the top surface 111 of the washer 110 and the underside 75 of the head 71 of a bolt after they were placed adjacent to each other and subjected to 1100° C. for 30 minutes.

Diffusion bonding of the bolts to the washer may be done as an independent operation or as a part of the manufacturing of the overall structure. In either case the bolts are passed through apertures in the same washer and threaded into a first high temperature material in such a way as to secure a second high temperature material to the first. One embodiment is when bolts are threaded into the collector of an X-ray tube constructed of a first high temperature material to secure a heat shield constructed of a second high temperature material to the collector. Typically the bolts pass through the second high temperature material after first passing through the washer and before being threaded into the first high temperature material. The bolts are threaded into the first high temperature material until the undersides of their heads contact the top surface of the washers. Then the bolts and washer are subjected to an elevated temperature for a sufficient time to cause mechanically detectable diffusion bonding between the bolts and the washer, i.e. diffusion bonding which can sustain a measurable mechanical load. The mechanically detectable diffusion can be detected and measured with a torque wrench. A typical bonding process for a nickel washer and molybdenum alloy bolts is about 1100° C. for about 30 minutes. This bonding process may be done as part of the procedure for the manufacture of an X-ray tube. The insert portion of an X-ray tube is built up. As part of this build up a collector is installed which has tapped holes. A heat shield is attached using bolts which pass through a common washer which has a separate through aperture for each bolt. The bolts are passed through the heat shield and into the tapped holes in the collector. The bolts are then drawn at least snug-tight against the washer. The vacuum envelope which is typically the outer boundary of the insert is then completed. Processing of the insert results in the collector being exposed to elevated temperatures, resulting in the diffusion bonding between the washer and bolt. The diffusion bonding provides a structure that is suitable for use in a vacuum environment and will not be the source of outgassing which would contaminate the vacuum. The diffusion bonding provides both adequate torque retention to ensure the bolts remain secured within the structure at the high temperature environment as well as ensuring that the means used to provide a secondary torque retention over the use of the threads do not contaminate the vacuum environment when the structure is at temperatures at or above 500° C. or as otherwise noted above herein. The diffusion bonding of the bolts and washer as described herein does not introduce chemicals into the vacuum environment at operating temperature above 500° C. or as otherwise noted above herein.

The diffusion bonding may be weak enough to allow the removal of the bolts by fracture of these bonds but alternatively the washer may be provided with a region of weakness between adjacent apertures that allows the removal of a bolt by applying a reverse torque to the bolt head which causes a fracture of the of the washer through this region. This alternative provides fairly reproducible control of the force necessary to remove a bolt, particularly if the weakness is provided by eliminating some of the material of the washer.

It may be of value to be able to readily remove bolts that have diffusion bonded to a washer. This facilitates to ability to do rework in the construction of an X-ray tube. If needed rework were to require the removal of the heat shield from the collector the ability to remove its securing bolts by fracturing the retaining washer through its area of weakness would be of value. It would allow one to remove the heat shield with less chance of damage. The bolts as described herein at the operating temperature retain their structural integrity in such a manner that the shape of the bolts are not compromised to the extent that the torque between the bolts and collector is not completely degraded. The bolt material provides for resistance to creep at temperatures over 500° C.; good surface stability; and/or corrosion and oxidation resistance. The materials of the bolts being selected to maintain sufficient pretension of the bolt and collector of a predetermined value.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. The term metal or metals as used herein with contemplates and includes alloys of the same metal. In another embodiment washer may include a member extending therefrom that is prohibits rotation of the washer by engaging a feature of a surface of the member that the washer is adjacent to. In this manner, the washer may only be removed by fracturing the washer body and or completely removing the bolt or other fastener from the opening of the washer. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A fastening assembly for high temperature components comprising:
    at least two fasteners each having a head with an underside and an elongated shaft extending therefrom and comprising at least one of a refractory metal and a superalloy; and
    a washer having a body with an upper surface, an opposing lower surface, and defining a first opening and a second opening for receiving therethrough the elongated shafts of the at least two fasteners,
    wherein the at least two fasteners and the washer are configured to secure a first high temperature material to a second high temperature material by securing the elongated shafts of the at least two fasteners to the first high temperature material, and the upper surface of the washer forms diffusion bonds with the underside of the respective head of the at least two fasteners when the washer and the at least two fasteners are held in contact at temperatures in excess of 500° C.

2. The fastening assembly of claim 1 wherein the first high temperature material is a collector for back scattered electrons in a high energy X-ray tube and the second high temperature material is a heat shield for the insert window of the X-ray tube.

3. The fastening assembly of claim 2 wherein the second high temperature material is graphite.

4. The fastening assembly of claim 3 wherein the first high temperature material comprises molybdenum or a molybdenum alloy.

5. The fastening assembly of claim 1 wherein the at least two fasteners comprise molybdenum or a molybdenum alloy.

6. The fastening assembly of claim 5 wherein the washer comprises nickel or a nickel alloy.

7. The fastening assembly of claim 1 wherein the washer has an area of weakness in a region between a first opening and the second opening configured to facilitate a fracturing of the washer in a region between the two openings when an external torque is applied to at least one of the at least two fasteners.

8. The fastening assembly of claim 7 wherein the at least two fasteners are threaded bolts.

9. The fastening assembly of claim 1 wherein the at least two fasteners are threaded bolts.

10. An assembled structure suitable for use at high temperatures comprising:
    at least two bolts, each bolt having a head with an underside and an elongated shaft extending from the underside, each bolt comprising at least one of a refractory metal and a superalloy;
    a washer having a body with an upper surface and an opposing lower surface defining at least a first aperture and a second aperture respectively receiving the shaft of at least the first bolt and the shaft of the second bolt;
    a first high temperature material into which the at least two bolts have been threaded; and
    a second high temperature material which has been secured to the first high temperature material by the at least two bolts;
    wherein the underside of the head of each bolt has mechanically measurably diffusion bonded to the upper surface of the washer.

11. The assembled structure of claim 10 wherein there is no mechanically cognizable diffusion bonding between the bolts and the threads of the first high temperature material into which each bolt is threaded.

12. The assembled structure of claim 10 wherein there is no mechanically cognizable diffusion bonding between the washer and the second high temperature material.

13. The assembled structure of claim 10 wherein the threading of the bolts into the first high temperature material does not cause the elastic compression of the second high temperature material.

14. The assembled structure of claim 10 wherein the structure is suitable for use in a closed vacuum and will not be the source of outgassing which would contaminate the vacuum.

15. The assembled structure of claim 10 wherein the first high temperature material is a collector for back scattered electrons in a high energy X-ray tube, the second high temperature material is a heat shield for the insert window of the X-ray tube and the structure is inside an evacuated insert of an X-ray tube.

16. A process for securing a heat shield for an insert window of a high energy X-ray tube to a collector for back scattered electrons comprising:
    providing a fastener having a head with a member extending therefrom, the member comprising at least one of a refractory metal and a superalloy;
    providing a washer having a body with an upper surface and an opposing lower surface which defines at least a first opening for receiving the member of the fastener therethrough;
    passing the fastener through the first opening of the washer and securing the member by threading the fastener into a first member to form an assembled structure; and
    subjecting the assembled structure to a high temperature to cause the fastener to diffusion bond to the washer to a mechanically detectable degree.

17. The process of claim 16 wherein: (i) the fastener is a bolt having a head and a threaded elongated member threadably received within a collector, (ii) the washer defines a second opening region to receive an elongated member of a second bolt, the elongated member being threadably received within a second threaded region of the collector, the second bolt being diffusion bonded to the washer, and (iii) each bolt and the collector are constructed of molybdenum or a molybdenum alloy, the heat shield is composed of graphite, the washer is constructed of nickel or a nickel alloy and retain the diffusion bond at temperatures over 500° C.

* * * * *